(12) United States Patent
Evers et al.

(10) Patent No.: US 10,466,163 B2
(45) Date of Patent: Nov. 5, 2019

(54) CONCURRENTLY EVALUATING ASSAYS WITH OPTICAL INHOMOGENEITIES

(75) Inventors: Toon Hendrik Evers, Eindhoven (NL); Derk Jan Wilfred Klunder, Geldrop (NL); Jeroen Hans Nieuwenhuis, Waalre (NL); Joannes Baptist Adrianus Dionisius Van Zon, Waalre (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 606 days.

(21) Appl. No.: 14/113,964

(22) PCT Filed: Apr. 23, 2012

(86) PCT No.: PCT/IB2012/052028
§ 371 (c)(1),
(2), (4) Date: Oct. 25, 2013

(87) PCT Pub. No.: WO2012/147021
PCT Pub. Date: Nov. 1, 2012

(65) Prior Publication Data
US 2014/0051187 A1    Feb. 20, 2014

(30) Foreign Application Priority Data

Apr. 28, 2011    (EP) .................... 11164118

(51) Int. Cl.
*G01N 33/53*    (2006.01)
*G01N 21/00*    (2006.01)
(Continued)

(52) U.S. Cl.
CPC .......... *G01N 21/00* (2013.01); *G01N 21/552* (2013.01); *G01N 21/8851* (2013.01);
(Continued)

(58) Field of Classification Search
None
See application file for complete search history.

(56) References Cited

U.S. PATENT DOCUMENTS 4,989,973 A * 2/1991 Noso ................. G01N 21/94
356/239.8
5,331,396 A * 7/1994 Yukawa ............. G01N 21/94
356/239.8
(Continued)

FOREIGN PATENT DOCUMENTS

CN    101655462 A    2/2010
DE    102009003548 A1    9/2010
(Continued)

*Primary Examiner* — Christopher L Chin

(57) ABSTRACT

During an assay, optical measurements are made at a sensing surface (112), and at least one "homogeneity-image" of the sensing surface (112) is generated. From this image, an "homogeneity-indicator" is determined for at least one region of interest, and the optical measurements are then evaluated in dependence on said indicator. The homogeneity-indicator may for example be a binary value which indicates if an inhomogeneity was detected or not. If an inhomogeneity was detected, all optical measurements may be rejected, only measurements for the involved region of interest may be rejected, or measurements for a selected sub-area of the involved region of interest (ROI) may be rejected.

12 Claims, 3 Drawing Sheets

(51) Int. Cl.
- *G01N 21/552* (2014.01)
- *G01N 21/88* (2006.01)
- *G01N 21/94* (2006.01)
- *G06T 7/00* (2017.01)
- *G01N 33/52* (2006.01)
- *G01N 21/15* (2006.01)

(52) U.S. Cl.
   CPC .......... *G01N 21/94* (2013.01); *G06T 7/0012* (2013.01); *G01N 33/52* (2013.01); *G01N 2021/157* (2013.01); *G06T 2207/30072* (2013.01); *G06T 2207/30168* (2013.01)

(56) References Cited

U.S. PATENT DOCUMENTS

| | | | |
|---|---|---|---|
| 5,790,691 A * | 8/1998 | Narayanswamy | G06K 9/00127 382/133 |
| 5,907,396 A * | 5/1999 | Komatsu | G01N 21/94 356/237.1 |
| 6,055,060 A | 4/2000 | Bolduan | |
| 6,175,645 B1 * | 1/2001 | Elyasaf | G01N 21/8806 356/237.4 |
| 7,410,613 B2 * | 8/2008 | Iwaki | G01N 21/5907 422/82.05 |
| 8,160,348 B2 * | 4/2012 | Pinard | G06K 9/00127 349/79 |
| 2003/0043550 A1 | 3/2003 | Ives | |
| 2005/0014174 A1 | 1/2005 | Burmeister | |
| 2005/0110989 A1 | 5/2005 | Schermer | |
| 2005/0153290 A1 | 7/2005 | Van Beuningen | |
| 2008/0181458 A1 | 7/2008 | Okawa | |
| 2009/0074285 A1 | 3/2009 | Fujimori | |
| 2011/0311962 A1 | 12/2011 | Zybin | |
| 2012/0250005 A1 | 10/2012 | Schleipen et al. | |

FOREIGN PATENT DOCUMENTS

| | | |
|---|---|---|
| JP | 2007017282 A | 1/2007 |
| WO | 2003021853 A2 | 3/2003 |
| WO | 2008072156 A2 | 6/2008 |
| WO | 2008142492 A1 | 11/2008 |
| WO | 2008155716 A1 | 12/2008 |
| WO | 2009001276 A1 | 12/2008 |
| WO | 2009125339 A2 | 10/2009 |
| WO | 2011027291 A1 | 3/2011 |

* cited by examiner

CONCURRENTLY EVALUATING ASSAYS WITH OPTICAL INHOMOGENEITIES

CROSS-REFERENCE TO PRIOR APPLICATIONS

This application is the U.S. National Phase application under 35 U.S.C. § 371 of International Application No. PCT/IB2012/052028, filed on Apr. 23, 2012, which claims the benefit of European Application No. 11164118.9, filed Apr. 28, 2011. These applications are hereby incorporated by reference herein.

FIELD OF THE INVENTION

The invention relates to a method for evaluating an assay comprising the generation of images of a sensing surface. Moreover, it relates to a sensor device for performing and evaluating such an assay.

BACKGROUND OF THE INVENTION

The U.S. Pat. No. 7,410,613 B2 discloses an apparatus in which different spots resulting from a blood test are imaged by an image sensor. To deal with nonuniformities of spots and/or with fine dust in the reaction area, the detected light intensities in a plurality of sub-areas of a spot are statistically processed to yield their mean value, median value, or normal distribution.

SUMMARY OF THE INVENTION

It is an object of the invention to provide means that allow for a more accurate evaluation of measurements which may be impaired by inhomogeneities.

According to its first aspect, the invention relates to a method for evaluating an assay that is performed with a sample, for example with a biological material like blood or saliva. The term "assay" is to be understood here in a quite general sense, comprising in the most simple case the mere provision of a sample for measurements. In many cases, an assay will however comprise some processing of the sample, for example its incubation with reagents, the binding of substances from the sample to probes or the like. The method comprises the following steps:

a) Making optical measurements at a surface, which will be called "sensing surface" in the following and which is (or can be) contacted by the sample. The optical measurements shall include the generation of at least one image of the sensing surface, wherein this image is called "homogeneity-image" in the following (because it is evaluated with respect to homogeneity-aspects).

b) Determining an indicator of the image homogeneity within at least one region of interest in the aforementioned homogeneity-image. This indicator will be called "homogeneity-indicator" in the following. The "image homogeneity" of an image region refers to the spread of image values (e.g. gray values in case of a grayscale image), wherein a completely homogeneous image would be monochrome with a single image value only. The homogeneity-indicator may be a binary variable or value that just expresses if a considered region of interest is homogenous or not (according to some given definition or threshold). It may however also be a multi-valued or even continuous variable by which the degree of homogeneity can be quantified. The homogeneity-indicator may for example correspond to the difference between the minimal and the maximal image value occurring in the region of interest.

c) Evaluating the optical measurements made at the sensing surface in dependence on the aforementioned (at least one) homogeneity-indicator.

It should be noted that the "homogeneity-image" is usually generated during a non-transient phase of an assay, or, with other words, that the "homogeneity-indicator" typically captures non-transient inhomogeneities. In this context, a phase or an inhomogeneity is considered as being "transient" if it lasts at most for several (say 5) seconds. An example would be the transient image inhomogeneity caused by a moving liquid meniscus. The inhomogeneities that are of interest in the context of the present invention, on the contrary, will typically last longer, i.e. for more than 10 s, 60 s etc. or even for the whole duration of an assay.

According to a second aspect, the invention relates to a sensor device for performing and evaluating an assay with a sample, particularly according to a method of the kind described above. The sensor device comprises the following components:

a) A carrier in which a sample can be provided (accommodated), said carrier having a sensing surface which can be contacted by the sample. The carrier may for example be a disposable cartridge that is used for a single measurement with a (biological) sample.

b) An optical sensor unit for making optical measurements at the aforementioned sensing surface, said sensor unit comprising an image sensor by which images of the sensing surface can be generated. In many cases, the optical sensor unit will consist of this image sensor, though it may optionally also comprise further components (e.g. a light source, a spectrometer, etc.).

c) An evaluation unit that is coupled to the optical sensor unit and that may be realized by dedicated electronic hardware, digital data processing hardware with associated software, or a mixture of both. The evaluation unit is adapted to:
  determine an indicator of the image homogeneity within at least one region of interest of a "homogeneity-image" of the sensing surface that was generated by the image sensor;
  evaluating the optical measurements provided by the optical sensor unit in dependence on said homogeneity-indicator.

As the method and the sensor device defined above are tightly related, definitions and explanations provided for one of them are analogously applicable to the other one. The method and the sensor device are based on the idea that one or more "homogeneity-indicators" are determined from at least one ("homogeneity-") image of a sensing region, and that the evaluation of optical measurements during an assay should be based on the results of this determination. Hence the sensing surface (or a region of interest therein) is explicitly checked with respect to a possible (optical) inhomogeneity, which is often caused by effects that also affect the measurements or the assay (e.g. an improper coating of binding sites, a contamination with dirt or the like). If such inhomogeneities are detected, appropriate measures can be taken in order to guarantee the validity and accuracy of the performed optical measurements. This approach allows to achieve much better results than the procedures known from the state of the art, for example from the U.S. Pat. No. 7,410,613 B2, in which inhomogeneities are not separately detected but processed to a mean value or the like.

In the following, various preferred embodiments of the invention will be described that relate to both the sensor device and the method described above.

According to first preferred embodiment, the assay to which the method and the sensor device refer may comprise the specific binding of target components of a sample to at least one binding spot on the sensing surface. The accumulation of the target components at a binding spot may then optically be detected, which allows to determine the presence and/or the amount of target components in the sample. The accuracy of such a measurement can be corrupted if the binding spots are not uniform, for example because they are not evenly coated with binding sites, because they are contaminated by dirt or the like. These situations can however be detected if the homogeneity-indicator is determined in a region of interest above the binding spot.

The aforementioned target components may particularly be labeled by magnetic particles, which allows to manipulate them by magnetic forces. Hence the binding process can be accelerated and/or unbound components can magnetically be washed away from the sensing surface before a measurement. More details about such assays and appropriate optical measurements are for example described in the WO 2008/155716 A1, WO 2009/125339 A2, WO 2009/001276 A1, or WO 2008/142492 A1, which are incorporated into the present application by reference.

The optical measurements at the sensing surface may preferably comprise or completely consist of the generation of a plurality of images of the sensing surface. Hence the image sensor that is used to produce the homogeneity-image can also be used to provide the optical measurements or at least a part thereof. In particular, the homogeneity-image can just be one of the optical measurements.

In one embodiment of the invention, the homogeneity-indicator may be determined by a feature detection procedure operating on the homogeneity-image. The feature detection procedure may for example identify non-uniform image structures that originate from gas bubbles at the sensing surface. When suspect features are detected in a region of interest, the corresponding homogeneity-indicator may be set to a value indicating the presence of an inhomogeneity.

According to another embodiment of the invention, the homogeneity-indicator may be determined from a histogram of image values in the region of interest. As known to a person skilled in the art, a histogram represent the frequency with which certain image values (e.g. gray values between 0 and 255) occur within the region of interest. If this region is homogeneous, the corresponding histogram has a sharp (ideally single-valued) peak. Deviations from this kind of histogram will hence be an indicator of image inhomogeneities. In particular, the region of interest may be assumed to be inhomogeneous if its histogram has more than one peak.

In still another embodiment of the invention, the homogeneity-indicator is determined from a comparison of the homogeneity-image with reference data, particularly from a comparison with one or more reference images of the region of interest. The reference images may for example be images of cartridges which are known to function well. Moreover, the comparison may especially comprise a comparison (or, more specifically, a subtraction) of histograms of the measured homogeneity image and the reference image.

Depending on the type of assay, there may be different times at which an homogeneity-image should be generated. An homogeneity-image may particularly be generated at these start of the assay, the end of the assay, or during the ongoing assay. Of course it is also possible to generate a plurality of homogeneity-images at different times of an assay.

If more than one homogeneity-indicator is determined for an assay, the evaluation of optical measurements may be based on a comparison of these. In particular, homogeneity-indicators (typically for the same region of interest) of homogeneity-images generated during different phases of the assay may be compared. Different phases of an assay may give rise to the appearance or disappearance of certain distortions. The corresponding change in the homogeneity-indicators will hence often allow to infer which kind of distortion is present.

The aforementioned different phases of the assay may particularly include phases before and after a wetting of the sensing surface with a sample occurs. Such a wetting nearly always occurs in assays in which a liquid sample is used, because this sample must, as a first step, be introduced into the space where the measurements take place. Hence there will usually always be an opportunity to observe and compare phases before and after such a wetting. As was already explained above, the change of the homogeneity-indicator during wetting allows some conclusions about the possible kinds of distortion, for example:

If an initially present inhomogeneity vanishes during wetting, this may be due to irregularities within a soluble component, for example due to cracks in a protective sucrose layer above binding spots.

If an inhomogeneity appears during wetting, this may be due to the presence of dirt or gas bubbles in the sample.

If an inhomogeneity remains unchanged during wetting, it may be caused by disturbances in the optical path, for example by dirt or scratches on optical windows.

If the determined homogeneity-indicator of at least one region of interest deviates from a given target range of "normal" or "allowable" values, this can have different consequences for the evaluation of the optical measurements. Optical measurements may for instance be rejected, i.e. not be taken into account as valid values. In particular, all optical measurements may completely be rejected if an inhomogeneity was detected anywhere on the sensing surface. Alternatively, only those measurements may be rejected that refer to the respective region of interest in which the homogeneity-indicator deviated from the target range (while optical measurements for other regions may still be used). Finally, the rejection may only refer to a sub-area of the affected region of interest. Parts of this region that are sufficiently homogeneous may in this case still contribute to the final measurement results obtained for the assay.

The aforementioned rejection of optical measurement (only) for a sub-area of a region of interest requires an appropriate procedure to discriminate between rejected and accepted parts of said region of interest. In particular, the sub-area of the region of interest that is rejected can be identified by a deviation of its image values from a given range of image values. If normally the region of interest should for example have gray values from some given interval, those parts (pixels) of the region of interest that have image values outside this interval might be rejected from the evaluation.

The method according to the invention will typically be realized with the help of a computing device, e.g. with a microcontroller or a personal computer. Accordingly, the present invention further includes a computer program product which provides the functionality of any of the methods according to the present invention when executed on a computing device.

Further, the present invention includes a data carrier, for example a floppy disk, a hard disk, an EPROM, or a compact disc (CD-ROM), which stores the computer product in a machine readable form and which executes at least one of the methods of the invention when the program stored on the data carrier is executed on a computing device. The data carrier may particularly be suited for storing the program of the computing device mentioned in the previous paragraph.

Nowadays, such software is often offered on the Internet or a company Intranet for download, hence the present invention also includes transmitting the computer product according to the present invention over a local or wide area network.

The invention further relates to the use of the sensor device described above for molecular diagnostics, biological sample analysis, chemical sample analysis, food analysis, and/or forensic analysis. Molecular diagnostics may for example be accomplished with the help of magnetic beads or fluorescent particles that are directly or indirectly attached to target molecules.

BRIEF DESCRIPTION OF THE DRAWINGS

These and other aspects of the invention will be apparent from and elucidated with reference to the embodiments described hereinafter.

In the drawings.

DETAILED DESCRIPTION OF EMBODIMENTS

In the following, the invention will be described with respect to biosensors based on nanoparticle labels, particularly based on magnetic beads that can be actuated with electromagnetic fields. Particular examples are biosensors for rapid handheld cardiac testing that allow the detection of cardiac troponin to diagnose myocardial infarct, or handheld parathyroid hormone (PTH) testing products that allow the detection of PTH for interoperative monitoring. It should however be noted that the invention is not restricted to these applications but can be used for sample examination in general.

Figure 1:
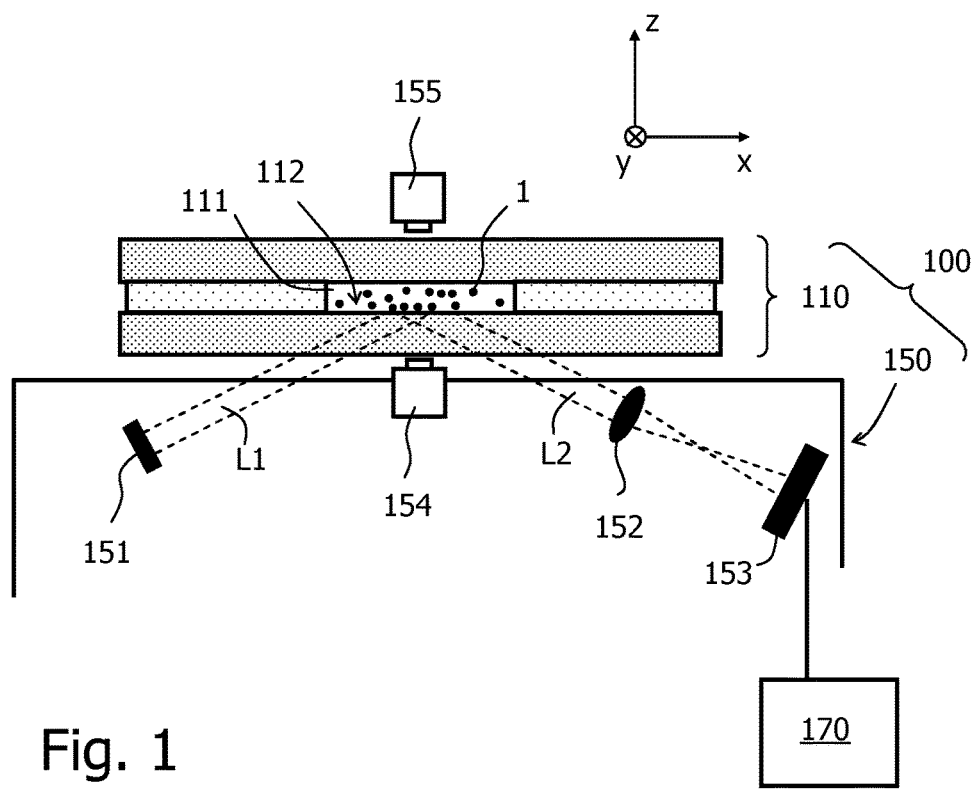
FIG. 1 schematically shows a side view of a sensor device according to the present invention.

FIG. 1 shows schematically a side view of a sensor device 100 according to the present invention. This sensor device 100 comprises an exchangeable (disposable) carrier or cartridge 110 with a sample chamber 111 in which a liquid sample can be provided next to a sensing surface 112. Moreover, the sensor device comprises an analyzer 150 with which optical measurements can be made at the sensing surface (if the cartridge 110 is properly placed on or in the analyzer). The analyzer 150 comprises an optical sensor unit with a light source 151 (e.g. an LED) for emitting an input light beam L1 towards the sensing surface, a focusing lens 152, and an image sensor 153 (2D camera) for detecting an output light beam L2 returning from the sensing surface 112. The measurement data (image or pixel values) generated by the image sensor 153 are processed by an evaluation unit 170. Moreover, the analyzer 150 comprises magnets 154 and 155 for generating a magnetic field in the sample chamber 111.

Typically, the sample comprises magnetic beads 1 functionalized with antibodies that can bind a specific analyte molecule. The beads 1 are attracted to the sensing surface 112, where they can indirectly (by means of a captured analyte) or directly bind to capture probes (e.g. antibodies) printed on the surface. The number of bound beads is directly or inversely related to the amount of analyte molecules present in the sample. The beads can then be detected using any technique that is more sensitive to beads that are close to the surface. In the shown example, the detection technique is based on evanescent optical fields, namely frustrated total internal reflection (FTIR) as described e.g. in the WO 2008/155716 A1 in more detail.

In another detection principle, the cartridge/fluid interface may be illuminated with an input light beam as shown in FIG. 1, but the scattered light from the particles near the surface is detected directly using a high NA objective located below the cartridge.

Figure 2:
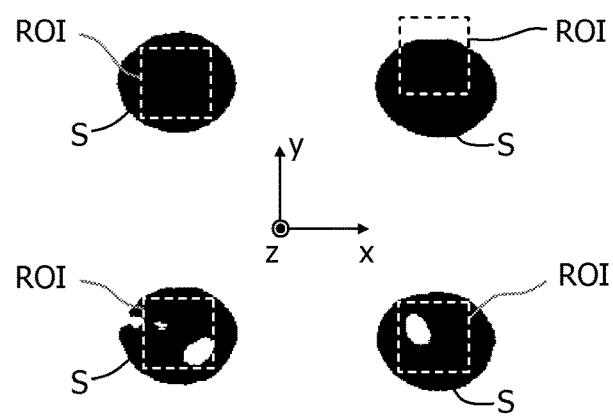
FIG. 2 shows exemplary images of binding spots together with the corresponding regions of interest where image values are evaluated.

After an assay executed with the sensor device 100, the darkness of the camera image in the spot S where capture probes (antibodies) have been printed is a measure of how many particles have been bound to the spot S. FIG. 2 shows in this respect four FTIR images of spots S after magnetic nanoparticles have been bound to the inkjet-printed antibodies. The rectangles "ROI" indicate the regions of interest in which the signal (i.e. the pixel values) are evaluated.

The top left image of FIG. 2 shows the desired case of a correctly positioned ROI in a relatively homogeneous spot S.

The top right image of FIG. 2 shows a misplaced ROI in a relatively homogeneous spot S.

The bottom images of FIG. 2 show spots S with clear inhomogeneities within the ROI.

Usually, the grayness inside a (rectangular) region of interest (ROI) is averaged to obtain the final result for a considered binding spot S. It is preferred that the ROI covers most of the spot, to enable averaging over more image pixels to obtain a more accurate result. However, it is possible that the ROI contains inhomogeneities in the amount of bound particles on the surface, resulting in an incorrect assay result. Such inhomogeneities in the ROI can be caused by many reasons, e.g.:

a misplacement of the ROI over the spot (FIG. 2, top right);

an inhomogeneous loading of antibodies within the spot (e.g. caused by formation of salt crystals during drying of the printed spots);

a partial damaging of the antibodies in the spot.

To prevent incorrect results, the present invention proposes to measure the homogeneity of the detected signal in the ROI before, during and/or after the assay. This measurement is done in at least one corresponding "homogeneity-image", and the result of this measurement is expressed as at last one "homogeneity-indicator". Based on these measurements (i.e. on the homogeneity-indicator(s)), the entire optical measurement, only certain spots, or only parts of the spots may be rejected.

This general approach will in the following be explained with respect to details of several preferred embodiments, relating to detecting inhomogeneities with different causes and at different times during the entire assay procedure.

In a first embodiment, sucrose layer defects can be detected. In a normal workflow, the cartridge 110 containing the antibody spots S and the dried nanoparticles is inserted into the analyzer 150 before the sample is added. Therefore, an (homogeneity-) image of the cartridge surface 112 before it has been wetted can be obtained. A cause of inhomogeneity in this dry state could be e.g. damage to the (plastic) sensor surface or the entrance and exit windows of the optical path through the cartridge. Another cause could be damage to the protecting layer that is usually applied to preserve the antibody activity using long-term storage. A typical agent for such a protecting layer is sucrose. If the sucrose layer is damaged, the antibodies underneath could be likewise damaged.

Figure 3:
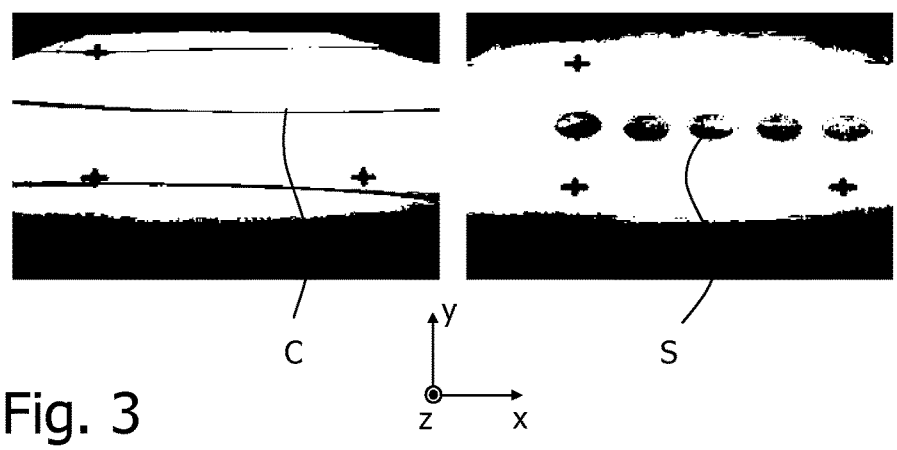
FIG. 3 shows images of a sensing surface with cracks in a protective sucrose layer before (left) and after (right) wetting by the sample fluid occurs.

FIG. 3 shows an example of a "crack" C in the sucrose layer over the area where the antibody spots are printed. The crack C is only visible in the dry state, i.e. before wetting of the sensing surface by the sample (FIG. 3 left). After wetting, the crack has vanished. The right image in FIG. 3 shows this state after the binding spots S have become visible due to bound magnet beads. The original position of the crack in the sucrose layer can still be seen as a lighter stripe over the antibody printed spots S, i.e. these areas show less binding of magnetic particles. These areas could be chosen to be excluded from the result calculations.

Figure 4:
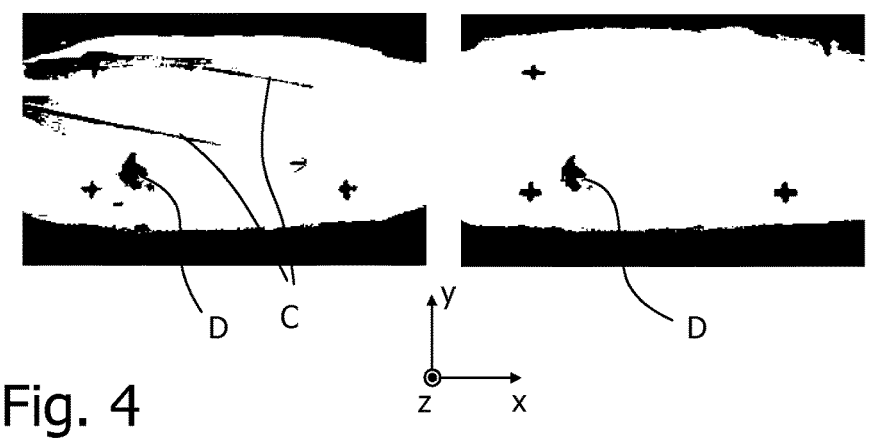
FIG. 4 shows images of a sensing surface with optical distortions before (left) and after (right) wetting by the sample fluid occurs.

In a second embodiment, defects in the optical path can be detected. This is illustrated in FIG. 4, which shows two FTIR images of a cartridge before (left) and after wetting by the sample (right).

As explained above, inhomogeneities C caused by the sucrose layer disappear after applying the sample. If inhomogeneities still exist, these could be caused by e.g. dirt or damages on the optical windows where the light beams enter/exit the cartridge (FIG. 1). FIG. 4 shows an example of such an inhomogeneity, namely a spot D of dirt, which can still be seen after the sample has been applied. In principle, such inhomogeneities should not have an effect on the amount of particles binding to the spot and can be compensated for as the final measurements outcome is calculated as a relative change with respect to the grey value before magnetic actuation. However, at very low signal changes, even e.g. a minute shift of the cartridge can result in a relatively large error if such an inhomogeneity is present in the ROI.

In principle, such an inhomogeneity could also be caused by e.g. dirt, damage to the surface (e.g. a scratch) or the like somewhere else in the optical path (analyzer windows, lenses, sensor etc.). This could indicate a need of servicing/cleaning the analyzer. It is possible to store the shape and location of the inhomogeneity in the analyzer, such that if the same inhomogeneity after wetting is observed during successive measurements, the analyzer indicates that servicing, cleaning, or replacing is in order.

Figure 5:
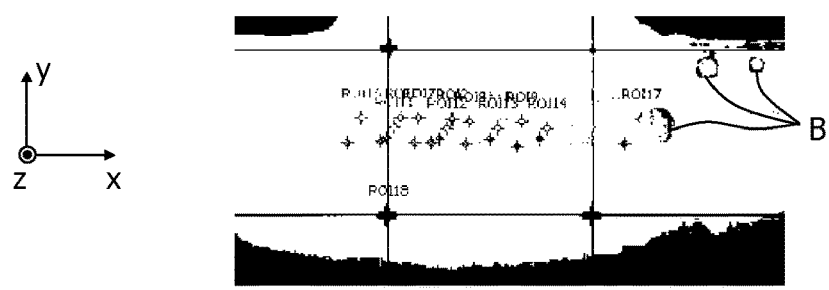
FIG. 5 shows an image of a sensing surface with air bubbles.

In a third embodiment, air bubbles can be detected. This is illustrated in FIG. 5, which shows an FTIR image with small air bubbles B, one close to a ROI.

The inclusion of air bubbles in the measurement chamber is another important cause of inhomogeneity in the image after wetting by the sample. With appropriate image processing algorithms, air bubbles B can be detected from a single image. Especially if there are small air bubbles on or close to the ROI (FIG. 5), these might not be detected using especially designed wetting detector structures, which are usually not present close to the ROI.

In a fourth embodiment, the homogeneity of particle density in the binding spot is determined. This is illustrated in FIG. 6, which shows a sketch of a spot S with an inhomogeneity (left) and a corresponding intensity histogram of the indicated ROI (right).

As shown in FIG. 2, there can be inhomogeneities in the particle density after magnetic particles have been bound to a binding spot S. These inhomogeneities can be detected by proper image processing algorithms, and the corresponding area can be excluded from the measurement, or the whole measurement can be rejected.

Figure 6:
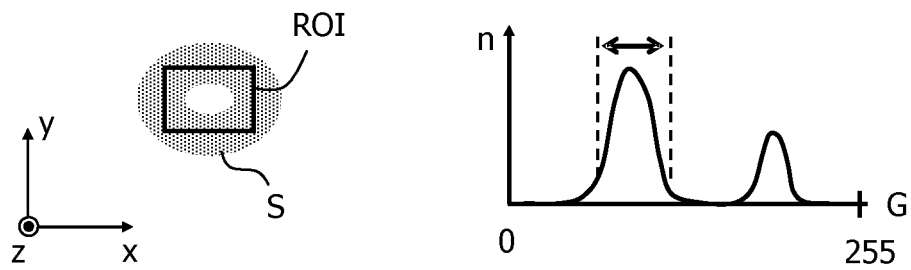
FIG. 6 illustrates the evaluation of an inhomogeneous region of interest with the help of a histogram.

A simple algorithm to achieve this is illustrated in FIG. 6. If a homogeneous spot S is subdivided in many smaller areas (with the smallest possible area being a single pixel on an image), a histogram of their intensities would yield a narrow distribution of gray values. However, if an inhomogeneity (e.g. a lighter area) is present, this would appear as an additional peak at different gray values (cf. FIG. 6 right). One possibility to detect or exclude the corresponding area is to set a threshold on the width of the detected main peak, such that all values that fall outside the threshold are not used to calculate the average gray value of the ROI. Of course, more advanced image processing algorithms that also take the position of the inhomogeneous areas into account could also be applied.

Figure 7:
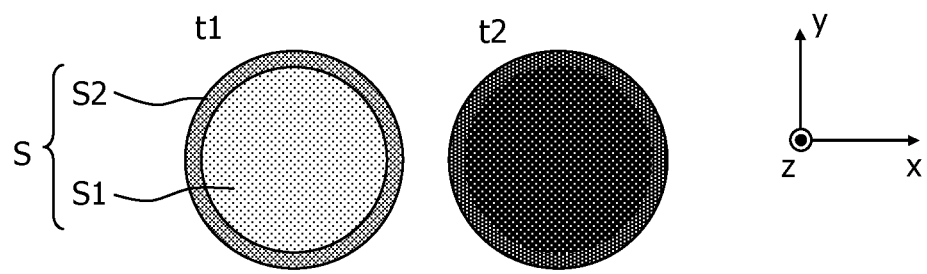
FIG. 7 illustrates an inhomogeneous binding spot at different phases of an assay.
Figure 8:
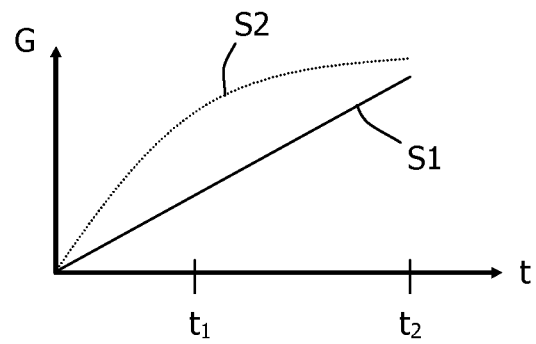
FIG. 8 shows the image values of the rim and the centre of the binding spot of FIG. 7.

It has to be noted that for all embodiments described above, an inhomogeneity detected in a particular image frame ("homogeneity-image") can be used to correct a result from a later or earlier frame in the measurement. In the situation shown in FIG. 7, a binding spot S consists of two areas: a main (center) area S1 and an outer rim S2. The different regions contain a different density of functional antibodies, resulting in different rates at which the particles will hind to the surface. Although at the end of the assay (time $t_2$) the signal change measured for the rim might fall within the predefined homogeneity threshold (as indicated in FIG. 6), a more accurate result could be obtained when not taking this rim into account. Because the signal in the rim saturates, the difference in signal between the two areas becomes very small at $t_2$. In an earlier point in time of the assay ($t_1$), the main area S1 could however be more clearly distinguished from the rim S2. This can be seen from. FIG. 7, which shows the image values G (e.g. gray values) of the rim and the center, respectively. The area containing the inhomogeneity (the outer rim) that is detected at $t_1$ could also be excluded in $t_2$.

Furthermore, an inhomogeneity does not need to be determined from a single frame/measurement, but could also be determined from assessing or averaging multiple (homogeneity-) images. For homogeneity detection during actuation of magnetic beads, a preferred time would be shortly after a "wash pulse", removing non-bound particles from the surface.

In summary, a non-homogeneous loading of an (inkjet-printed) spot of capture probes (e.g. antibodies) can result in an incorrect assay result in immunoassays. Methods to detect and to correct for such inhomogeneities and other inhomogeneities that can influence the measurement are provided by the present invention. To prevent incorrect results, it is proposed to measure the homogeneity of the detected signal in the ROI during the entire assay and to either correct for inhomogeneities in a given frame by only taking into account those areas that satisfy preset homogeneity requirements of all captured frames or, if certain homogeneity requirements are not met, reject the assay result.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A method for evaluating an assay of a sample on a sensing surface performed with an optical analyzer including at least an image sensor and a computer, said method comprising:
    generating at least one homogeneity-image of the sensing surface by imaging the sensing surface with the image sensor, the homogeneity-image including a plurality of pixels, each pixel having an image value;
    using a computer executing software:
        determining whether the image values of pixels in sub-areas of at least one region of interest (ROI) deviate from a given target range;
        in response to the image values of the pixels in one or more sub-areas deviating from the given target range, controlling the optical analyzer to one of:
            rejecting the assay with respect to a respective ROI in which the image values of the pixels in one or more sub-areas deviate from the target range, or
            rejecting the assay with respect to one or more sub-areas of the respective ROI in which the image values of the pixels deviate from the target range; and
        in response to the image values of the pixels in one or more sub-areas deviating from the given target range, assaying the sample based only on sub-areas of the respective ROI in which the pixels are within the given target range.

2. The method according to claim 1 wherein the assay comprises the specific binding of target components of the sample to at least one binding spot on the sensing surface.

3. The method according to claim 1, further including:
    generating a plurality of images of the sensing surface.

4. The method according to claim 1, wherein the determining of whether the image values of pixels in sub-areas of at least one region of interest (ROI) deviate from the given target range is determined by a feature detection procedure.

5. The method according to claim 1, wherein the determining of whether the image values of pixels in sub-areas of at least one region of interest (ROI) deviate from a given target range includes:
    generating a histogram of the image values of the pixels within the at least one region of interest (ROI); and
    determining whether the image values of the pixels in the sub-areas of at least one ROI deviate from the given target range based on whether a width of a main peak of the histogram falls within a given range.

6. The method according to claim 1, wherein the homogeneity image is generated at the start of the assay, an end of the assay, and during the assay.

7. The method according to claim 1, wherein determining whether the image values of pixels in sub-areas of at least one region of interest (ROI) deviate from a given target range includes:
    determining a shape and a location of an inhomogeneity present on the sensor surface, wherein the shape and location is stored as data on a data carrier, and wherein the shape and location data is readable by the data analyzer for subsequent determination of the deviation from the target range.

8. The method according to claim 1, wherein the optical analyzer further includes a light source, and the generating of the image includes emitting an input light beam toward the sensing surface using the light source.

9. The method according to claim 1, wherein the optical analyzer further includes magnets, the method further includes disposing magnetic beads at the sensing surface, and the generating of the image includes applying a magnetic field to the magnetic beads using the magnets.

10. The method according to claim 9, wherein the assaying comprises performing an assay to detect cardiac troponin.

11. The method according to claim 9, wherein the assaying comprises performing an assay to detect parathyroid hormone (PTH).

12. An assay method for evaluating an assay of a sample on a sensing surface performed with an optical analyzer including at least an image sensor and a computer, said method comprising:
    using the image sensor, generating at least one homogeneity-image of the sensing surface, the homogeneity-image including a plurality of pixels, each pixel having an image value; and
    using a computer executing software:
        determining whether the image values of pixels in sub-areas of at least one region of interest (ROI) deviate from a given target range, wherein the determining includes subtractively combining the homogeneity-image with a reference image of the ROI to generate a difference image and comparing pixels of the difference image to a given target image value; and
        in response to the image values of the pixels in one or more sub-areas deviating from the given target range controlling the optical analyzer to one of:
            reject the assay with respect to a respective ROI in which the image values of the pixels in one or more sub-areas deviate from the target range, or
            reject the assay with respect to one or more sub-areas of the respective ROI in which the image values of the pixels deviate from the target range; and
        in response to the image values of the pixels in one or more sub-areas deviating from the given target range, assaying the sample based only on sub-areas of the respective ROI in which the pixels are within the given target range.

* * * * *